United States Patent [19]

Child et al.

[11] 4,242,458

[45] Dec. 30, 1980

[54] BIOSYNTHESIS OF PROTEIN BY FERMENTATION OF METHANOL OBTAINED FROM THE GASIFICATION OF COAL OR RESIDUAL OIL

[75] Inventors: Edward T. Child, Tarrytown; Robert M. Suggitt, Wappingers Falls, both of N.Y.

[73] Assignee: Texaco Development Corporation, White Plains, N.Y.

[21] Appl. No.: 954,712

[22] Filed: Oct. 25, 1978

[51] Int. Cl.² ................... C12N 1/32; C12N 1/36; C12R 1/78
[52] U.S. Cl. ................... 435/247; 435/248; 435/804; 435/930

[58] Field of Search ............ 195/27, 28 R, 49; 435/247, 804, 248, 930

[56] References Cited

U.S. PATENT DOCUMENTS 4,145,445  3/1979  Hitzman .................. 195/49 X

*Primary Examiner*—Lionel M. Shapiro
*Attorney, Agent, or Firm*—Carl G. Ries; Robert A. Kulason; James F. Young

[57] ABSTRACT

This invention relates to a method of synthesizing single cell protein from residual oils and/or coal by a mutually advantageous combination of a synthesis gas generation process or a coal gasification process in the production of methanol and ammonia, and their use by the protein producing bacteria.

6 Claims, 1 Drawing Figure

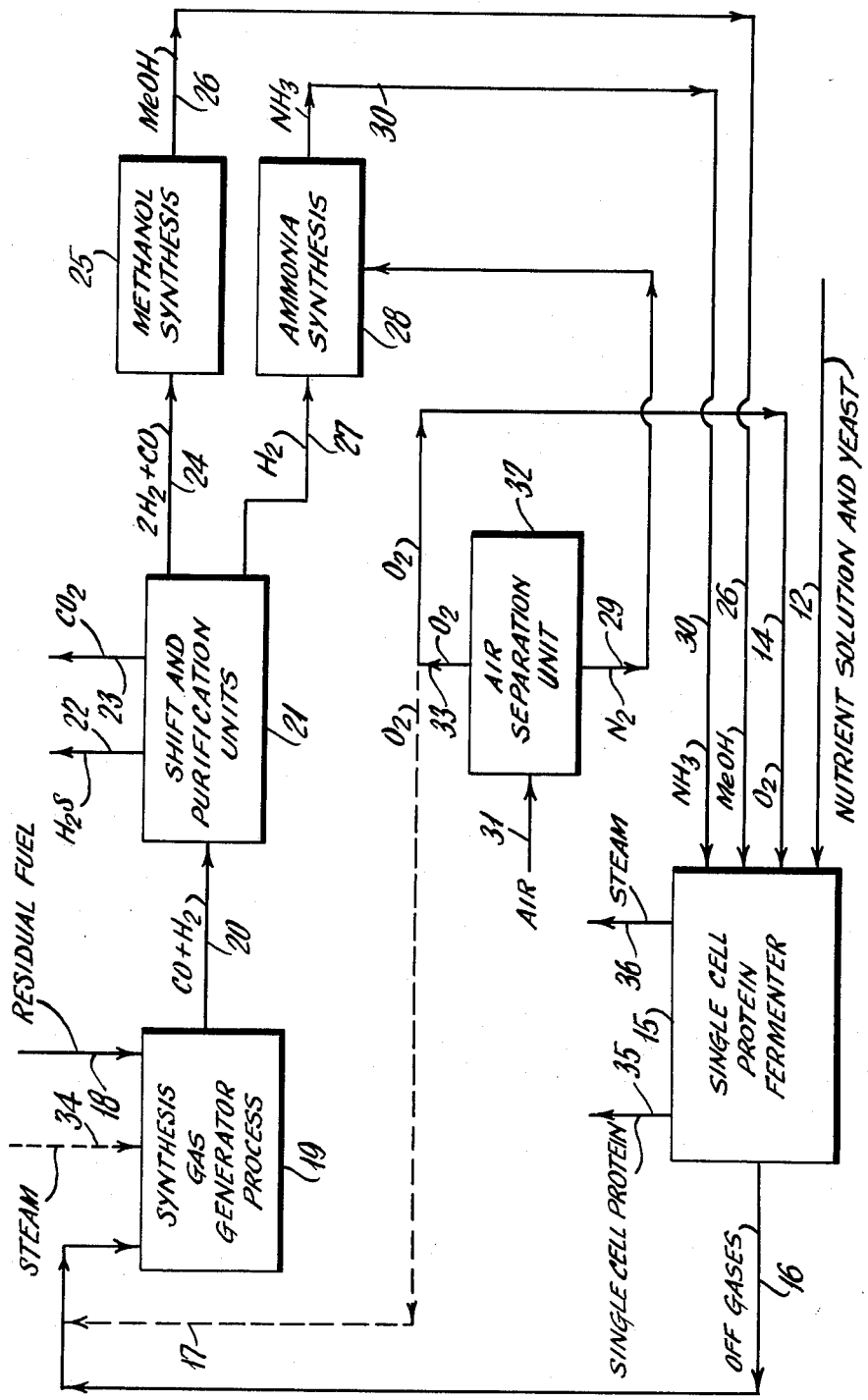

BIOSYNTHESIS OF PROTEIN BY FERMENTATION OF METHANOL OBTAINED FROM THE GASIFICATION OF COAL OR RESIDUAL OIL

SUMMARY OF THE INVENTION

The invention relates to a cyclic process for synthesizing protein from the end products of a synthesis gas generation process, or a coal gasification process, and the disposal of waste products from the protein production step by these partial oxidation facilities in a mutually advantageous manner.

BACKGROUND OF THE INVENTION

There is a mounting concern over future availability of food sources for the world's growing population. The incentive to grow single cell protein from petroleum hydrocarbons is a result of the fact that man is unable to feed himself under the present food distribution system, political climates, and in some locations, the use of poor methods of cultivation and low production of food. Two-thirds of the world's population of about 3.5 billion is reported to be hungry or malnourished. While about 80 million tons of protein are currently produced world-wide each year, the production of protein will have to double merely to keep pace with the world's population by the year 2000, assuming the present rate of growth is maintained.

Many energy sources for microorganisms cannot be used because of their possible inclusion of toxic or carcinogenic material from the substrate into the single cell protein product.

In particular, organic residues containing such toxic elements as copper, zinc, cadmium, tin, lead, arsenic, antimony, selenium, tellurium, nickel, cobalt, chromium, molybdenum, tungsten, vanadium, uranium, thorium and fluorine are avoided as substrates for food producing microorganisms. For example, it is known that cultures that grow on refinery waste effluents assimilate extremely low concentrations of chromium from solution. The fermentation media on which food forming cultures grow should be free of known toxic elements. Coal, for example, cannot be used as a microorganism energy source. Upwards of 40 elements, including several which are toxic, have been identified in coal.

Apart from a lack of aesthetic appeal, cultures grown on substrates containing these or other toxic elements can incorporate small quantities of these elements into the protein and thereby render the product unfit for consumption as a food for higher vertebrates.

Sources of energy in solid form, e.g. plastics and industrial wastes, coals, and coke are for practical purposes unavailable to microorganisms. The growth rate on these solid hydrocarbonaceous sources of energy is too slow to provide a practical way to generate protein. Separation of protein from unreacted solids also poses another obstacle to the use of this type of microorganism substrate. Gasification of these materials and their subsequent conversion into more reactive liquid and/or soluble forms of aliphatic substrates makes their energy content available to the microorganisms.

Microorganism substrate material preferably should be aliphatic compounds such as the linear aliphatic primary alcohols, n-paraffins containing 6 to 20 carbon atoms therein, the fatty acids, aldehydes and linear olefins. Such materials are preferably liquid at fermenter operating temperatures or possess at least limited solubility in the fermenter broth.

It is known to produce a carbon monoxide-hydrogen rich effluent stream from a synthesis gas generator by the partial oxidation of a hydrocarbonaceous fuel.

It is also known that the effluent from the synthesis gas generator can be treated to remove undesirable constituents such as hydrogen and carbon dioxide. Part of the purified effluent comprising carbon monoxide and hydrogen can be used in the synthesis of methanol, and part of the hydrogen employed in the production of ammonia.

It is further known that air can be separated into its major constituents, nitrogen and oxygen, by air rectification.

DESCRIPTION OF THE INVENTION

The present invention relates to an improved process for the production of single cell protein by the steps comprising:

(1) subjecting a carbonaceous fuel to partial oxidation to produce a gaseous stream of carbon monoxide and hydrogen, (2) passing a portion of the recovered gaseous stream from step 1 to a carbon monoxide shift converter to produce a stream of hydrogen, (3) passing the remaining portion of the recovered gaseous stream from step 1 to an acid gas scrubber to produce a purified stream of hydrogen and carbon monoxide, (4) introducing the purified stream of hydrogen and carbon monoxide from step 3 to a methanol synthesis unit to produce a stream of methanol, (5) separating air into its constituent elements of nitrogen and oxygen in an air rectification unit, (6) introducing separated oxygen from step 5 to the partial oxidation step 1, (7) introducing separated nitrogen from step 5 and the hydrogen recovered from step 2 into an ammonia synthesis unit to produce ammonia, (8) introducing the methanol from step 4, a portion of the separated oxygen from step 5, the ammonia from step 7, a nutrient solution comprising an aqueous solution of mixed inorganic salts and an initial charge of a Hansanula polymorpha DL 1 yeast, into a single cell protein fermenter, effecting production of single cell protein and off gases comprising carbon dioxide, oxygen, and water, (9) Passing at least part of the off gases containing oxygen and carbon dioxide from step 8 to the partial oxidation step 1 and,

(10) recovering single cell protein from step 8.

DESCRIPTION OF THE DRAWING

Reference is now made to the accompanying drawing in association with which an example of one method of practicing the present invention is disclosed. The single figure is a diagrammatic flow sheet representing an example of an arrangement of apparatus suitable for carrying out the process of the invention. It will be apparent to those skilled in the art that various pieces of equipment such as valves, compressors and the like for the sake of simplicity have been omitted from the drawing.

With reference to the accompanying drawing, a mixture of effluent gases 16 consisting of carbon dioxide, oxygen, and water is introduced into the Synthesis Gas Generation Unit 19. A stream of residual oil 18 is introduced into the Generator 19, along with an additional stream of oxygen 17, comprising a portion of oxygen stream 33, resulting from the air separation unit process. Optionally, a small steam stream 34 may be added to the Generator if the quantity of steam from the off gases is insufficient for the synthesis gas generation process.

The Synthesis Gas Generator 19 effects conversion of residual oil to synthesis gas by partial oxidation.

After the above streams are reacted in the Generator 19, the effluent stream 20 is fed into the Shift Conversion and Purification Units 21. A stream of acid gases including hydrogen sulfide 22, and a stream of carbon dioxide 23, are removed in the purification step.

A stream 24 consisting of hydrogen and carbon monoxide is introduced into the Methanol Synthesis Unit 25, in which carbon monoxide and hydrogen are synthesized into methanol.

A stream of air 31 is introduced into the Air Separation Unit 32, which is a conventional cryogenic unit effecting separation of air into its constituent parts. A portion of oxygen stream 33 is introduced into the Synthesis Gas Generation Unit 19, as stream 17.

Simultaneously with the introduction of the hydrogen and carbon monoxide stream into Methanol Synthesis Unit 25, a stream of hydrogen 27 from the Shift Converter 21, is fed into the Ammonia Synthesis Unit 28. A stream of nitrogen 29 resulting from the air separation unit process is also introduced into the Ammonia Synthesis Unit 28.

A stream of ammonia 30 is withdrawn from the Ammonia Synthesis Unit 28 and passed into the Single Cell Protein Production Unit 15.

A stream 26 of methanol from the Methanol Synthesis Unit 25 is passed into the Single Cell Protein Production Unit 15, and a portion of the oxygen stream 33 which is withdrawn from the Air Separation Unit 32, is introduced into the Single Cell Protein Production Unit 15 as stream 14.

A nutrient solution stream 12 is also introduced into Single Cell Protein Production Unit 15 with an initial charge of a Hansanula polymorpha DL 1 yeast. The Single Cell Protein Production Unit 15 converts the methanol, nutrient solution with the yeast, ammonia and oxygen, to single cell protein, steam and off gases.

There is withdrawn from Production Unit 15, a product stream 16 composed of a mixture of gases comprising carbon dioxide, oxygen and water. The off gases are compressed before being introduced into the Synthesis Gas Generation Unit 19, where the synthesis gas generation process is performed. A stream 35 of single cell protein is withdrawn. A separate steam stream 36 is also withdrawn from Unit 15.

DETAILED DESCRIPTION OF THE INVENTION

In the method of the invention a wide variety of hydrocarbonaceous fuels is suitable as feedstock for the partial oxidation step, either alone or in combination with each other or with particulate carbon. The hydrocarbonaceous feeds include fossil fuels such as liquid petroleum distillates, gas oil, fuel oil, residua, reduced crude, whole crude, synthetic crudes and fractions derived from oil shale, tar sands, and coal liquefaction products. Solid fuels include petroleum or coal coke, anthracite, semi-anthracite, bituminous, semi-bituminous, lignite coals and peat. In addition, suitable hydrocarbonaceous material includes forest products and wastes, agricultural products and wastes, manure, organic industrial products and wastes, including petrochemical and petroleum refining by-products, and sewage sludge.

A stream of oxygen from the Air Separation Unit, hereinafter described, is introduced into the generator.

In addition, off gases from the fermentation reactor, to be hereinafter described, are withdrawn from the Single Cell Protein Production Unit at near atmospheric pressures and compressed.

The Generator is maintained at 0.7 to 21 Megapascals (Mpa), at a temperature of 1000° C. to 1900° C., and the mixture is maintained therein for a period of 1 to 20 seconds to effect conversion of residual oil to synthesis gas by partial oxidation.

The $CO_2$ portion of the compressed residual mixture of $CO_2/O_2$ from the Single Cell Protein Production Unit, serves to moderate the partial oxidation reaction. In this way the temperature is reduced to a temperature not above about 1900° C. and preferably not above 1500° C. Thus, steam requirements for moderating the synthesis gas are reduced or eliminated. Also, no clean up of the fermenter off gas is required such as is needed if air off gas were vented to the atmosphere (e.g. to remove odoriferous material).

The free-oxygen containing gas and the additional compressed effluent gases along with the hydrocarbonaceous fuel are introduced separately into the generator through a burner comprising a central passage and an annular passage. The reactants are mixed with one another at the point of discharge from the burner into the synthesis gas generator.

The synthesis gas leaving the generator is quenched by water and this results in extremely rapid cooling, which freezes the composition of the product gas. Quenching of the gas by this particular method prevents the production of undesirable hydrocarbons in the fuel stream by synthesis during cooling, and prevents reactions leading to the formation of undesirable carbon dioxide and free carbon.

The synthesis gas effluent stream consisting essentially of hydrogen and carbon monoxide and containing less than about 2 percent residual methane by volume, is discharged from the synthesis gas generator to the saturator scrubber and then to the Purification Unit. In the saturator scrubber, the effluent synthesis gas stream is scrubbed to remove the acid gases, resulting in separate streams of hydrogen sulfide, carbon dioxide, carbon monoxide and hydrogen. The saturator scrubber is maintained at 0.7 to 21 Mpa.

Optionally, a portion of the raw synthesis gas may be water scrubbed to remove particulates and then passed to a Water-Gas Shift Unit. The carbon monoxide in the syngas reacts with water vapor in the presence of a catalyst such as cobalt-molybdenum on alumina to form hydrogen and carbon dioxide at a temperature of 260° C.–480° C. and a space velocity of 1000 to 4000 standard cubic meters per hour per cubic meter of catalyst. The product gas is then acid gas scrubbed separately (not mixed with the syngas that is to be used to make methyl alcohol) to remove carbon dioxide from (1) the expiration of the microorganisms, (2) the syngas generation reaction and (3) the water-gas shift reaction. The resultant purified gas is primarily hydrogen and can be used to synthesize ammonia or to increase the hydrogen content of the stream entering the Methanol Synthesis Unit.

The effluent stream from the Purification Unit consisting of hydrogen and carbon monoxide is introduced into the Methanol Synthesis Unit which is maintained at 10.4–17.3 Mpa and at a temperature of 221° C.–276° C. to effect synthesis of the carbon monoxide and hydrogen into methanol through a catalytic reaction.

An air mixture is introduced into the Air Separation Unit. A stream of oxygen and a stream of nitrogen are withdrawn.

A small portion of the oxygen withdrawn from the Air Separation Unit is introduced into the Synthesis Gas Generation Unit.

The nitrogen stream and a separate hydrogen stream are fed into the Ammonia Synthesis Unit. This unit is maintained at 14 to 31 Mpa and at a temperature of 450° C.–600° C.

Four streams are introduced into the Single Cell Protein Production Unit. These streams consist of a mixture comprising a first stream of methanol from the Methanol Synthesis Unit and a second stream comprising a nutrient solution of water and of salts. The salts which make up a small portion of the nutrient solution comprise KCl, 85% solution of $H_3PO_4$, $Na_2SO_4$, $FeSO_4.7H_2O$, $CaCl_2$, $ZnSO_4$, $H_3BO_3$, $CuSO_4.5H_2O$, $Na_2MoO_4.7H_2O$, and $NiCl_2.6H_2O$. The third stream introduced into the Single Cell Protein Production Unit consists of ammonia feed from the Ammonia Synthesis Unit and a fourth stream comprises oxygen from the Air Separation Unit.

After methanol, ammonia, oxygen, the nutrient solution and an initial charge of the yeast, Hansanula polymorpha DL 1, are introduced into the Single Cell Protein Production Unit, a process using continuous stirred tank fermenters and the main components for yeast growth is utilized. Fermentation tanks arranged in parallel are the main reactors and these are followed by one maturing reactor. The main reactors are filled to working capacity (80% filled) with the feed and nutrient solution, and the cells are allowed to grow and consume a major portion of the methanol before a stream of the fermentation broth is withdrawn continuously and fed to the maturing fermenter. The average residence time of material in the fermentation zone is 6.3 hours and about 1 hour in the maturing fermenter. The yeast grows aerobically at 37° C. with a growth rate of 0.15 gram per yeast per gram of methanol feed present per hour. The fermenter is maintained at atmospheric pressure.

The growth controlling factor is the methanol content within the growing fermenters. With continuous addition of methanol to the growing fermenters, the steady state methanol content is about 0.12 gram per liter. No methanol is added to the maturing fermenter. Methanol content should be limited to less than about 0.5 gram per liter in the growing fermenters since methanol at higher concentrations can inhibit growth of the yeast. If batch addition of methanol were used, the amount of methanol added would have to be carefully controlled in a series of reactors.

The single cell protein product has the following typical chemical composition per 100 grams:
47.0 grams combined carbon
6.5 grams combined hydrogen
7.5 grams combined nitrogen
31.0 grams combined oxygen
8.0 grams combined ash Mixed cultures of bacteria that are thermophilic can be used that grow on methanol with growth rates in the order of 0.45 gram per yeast per gram of methanol feed present per hour at temperatures of 50° C.–55° C. Yields of 0.42 gram of cells/gram of methanol are obtained with protein contents of 71%. With the higher operating temperatures (50°–55° C.), heat exchange is more efficient than with fermenters operating at 37° C.

A stream consisting of single cell protein and a separate stream consisting of steam are recovered from the Single Cell Protein Production Unit.

There is also withdrawn from the Single Cell Protein Production Unit, a product stream composed of a mixture of off gases comprising carbon dioxide, oxygen, and water. These off gases are compressed before being fed into the Synthesis Gas Generation Unit.

EXAMPLE

The invention is illustrated but not limited with reference to the following example.

A stream consisting of off gases is introduced into the Synthesis Gas Generation Unit. The off gases consist of $1.71 \times 10^5$ kg/day of carbon dioxide, $1.56 \times 10^5$ kg/day of oxygen and $0.07 \times 10^5$ kg/day of water. There is separately introduced an oxygen stream obtained from the Air Rectification Unit, hereinafter more fully described consisting of $0.04 \times 10^5$ kg/day. A stream of residual oil derived from an Arabian light crude which contains 5 ppm nickel and 27 ppm vanadium is also introduced in quantities of $1.58 \times 10^5$ kg/day.

The Synthesis Gas Generation Unit is maintained at 0.84 Mpa, at a temperature of about 1371° C., and the mixture is maintained therein for a period of 2.5 seconds to effect conversion of residual oil to synthesis gas by partial oxidation.

The effluent is fed into the Shift Conversion and Purification Unit which is maintained at 0.84 Mpa, at a temperature of 260° C.–480° C. and a space velocity of 1000 to 4000 standard cubic meters per hour per cubic meter of catalyst to effect conversion of said stream into carbon monoxide and hydrogen.

A stream consisting of $2.44 \times 10^5$ kg/day of hydrogen and carbon monoxide is introduced into the Methanol Synthesis Unit which is maintained at 10.4–17.3 Mpa and at a temperature of 221° C.–276° C. to effect synthesis of the carbon monoxide and hydrogen into methanol.

A mixture comprising $19.10 \times 10^5$ kg/day of air is introduced into the Air Separation Unit. A stream comprising $3.97 \times 10^5$ kg/day of oxygen and another stream comprising $0.0865 \times 10^5$ kg/day of nitrogen are withdrawn from the Air Separation Unit. A portion of a stream of oxygen from the Air Separation Unit is introduced into the Synthesis Gas Generation Unit in quantities of $0.04 \times 10^5$ kg/day.

A stream comprising nitrogen in quantities of $0.0865 \times 10^5$ kg/day resulting from the Air Separation Unit is introduced into the Ammonia Synthesis Unit. In addition, a stream of hydrogen from the Shift and Purification Unit, consisting of $0.0185 \times 10^5$ kg/day is fed into the Ammonia Synthesis Unit. The Ammonia Synthesis Unit is maintained at 14 to 31 Mpa and at a temperature of 450° C.–600° C.

Four streams are introduced into the Single Cell Protein Production Unit. These streams consist of a mixture comprising a first stream of $2.44 \times 10^5$ kg/day of methanol from the Methanol Synthesis Unit and a second stream comprising a nutrient solution of $4.45 \times 10^5$ kg/day of water and $0.10 \times 10^5$ kg/day of salts. The salts which make up a small portion of the nutrient solution comprise 1700 kg/day of KCl, 8500 kg/day of 85% solution of $H_3PO_4$, 400 kg/day of $Na_2SO_4$, 15 kg/day of $FeSO_4 \cdot 7H_2O$, 300 kg/day of $MgSO_4 \cdot 7H_2O$, 15 kg/day of $MnSO_4 \cdot 7H_2O$, 1.0 kg/day of $CaCl_2$, 200 grams/day of $ZnSO_4$, 200 grams/day of $H_3BO_3$, 200 grams/day of $CuSO_4 \cdot 0.5H_2O$, 40 grams/day of $Na_2MoO_4 \cdot 7H_2O$ and 6 grams/day of $NiCl_2 \cdot 6H_2O$. The third stream introduced into the Single Cell Protein Production Unit consists of $10.5 \times 10^3$ kg/day of ammonia feed from the Ammonia Synthesis Unit and a fourth stream comprises $3.97 \times 10^5$ kg/day of oxygen from the Air Separation Unit. The Production Unit is maintained at atmospheric pressure and at a temperature of 37° C. The mixture is maintained therein for a period of 6.3 hours to effect conversion to single cell protein, steam and off gases.

There is withdrawn from the Single Cell Protein Production Unit, a product stream composed of a mixture of gases comprising $1.71 \times 10^5$ kg/day of carbon dioxide, $1.56 \times 10^5$ kg/day of oxygen and $0.07 \times 10^5$ kg/day of water.

The off gases are compressed before being fed into the Synthesis Gas Generation Unit.

There is also withdrawn from the Single Cell Protein Production Unit, a stream consisting of $1.00 \times 10^5$ kg/day of single cell protein and a separate stream consisting of $6.72 \times 10^5$ kg/day of steam.

The efficiency of the above described cyclic system is apparent since the oxygen and carbon dioxide contents of the off gases leaving the Single Cell Protein Production Unit are almost exactly the amounts required as oxidant and moderator, respectively, for the Synthesis Gas Generation Unit. Thus the waste oxygen and carbon dioxide from the Single Cell Protein Production Unit become valuable charge materials to the Synthesis Gas Unit, and only very small amounts, if any, of expensive oxygen and steam are required to properly maintain the reactions in the Synthesis Gas Unit. Also, concentrated waste waters as well as undesirable by-products in the off-gas stream from the Single Cell Protein Production Unit, can be disposed of by charging them to the Synthesis Gas Generation Unit in an environmentally acceptable manner. The overall effect is that expensive oxidant and moderator components for the Synthesis Gas Unit, used to manufacture the methanol and ammonia required in the fermentation step, are replaced by undesirable by-products from the fermentation reaction, also resulting in large savings in the fermentation waste product disposal system.

The unexpected advantages of the process of this invention are in the synthesis gas generation step. The following effects should be noted:

1. heavy material is gasified thus destroying carcinogenic compounds.
2. toxic elements such as nickel, vanadium in petroleum residue, or cadmium, lead, or chromium in coal or industrial wastes, exit from the generator in molten slag or as solids.
3. The syngas is cooled and scrubbed to remove particulate material containing any traces of entrained toxic metals. This removes the $CO_2$ formed by the expiration of the micro organisms and the carbon dioxide produced in the partial oxidation reactor. Also sulfur is removed in the form of hydrogen sulfide and carbonyl sulfide. Selenium is removed as hydrogen selenide. Any traces of halides, e.g., HCl, HF, that passed through the particulate scrubbing section are removed.

Obviously, many modifications and variations of the invention as hereinabove set forth may be made without departing from the spirit and scope thereof, and therefore only such limitations should be imposed as are indicated in the appended claims.

We claim:

1. A process for the production of single cell protein which comprises the steps of:
    (a) subjecting a carbonaceous fuel comprising a liquid hydrocarbon fuel of petroleum distillates or residua, naphtha, gas oil, residual fuel, reduced crude fuel oil, whole crude, coal tar oil, shale oil, coal liquefaction products and mixtures thereof, or solid fuels of petroleum coke, coal coke, anthracite, bituminous coal, lignite, or gaseous fuels of natural gas, to partial oxidation with an oxygen-containing material to produce a product gas containing carbon monoxide and hydrogen,
    (b) passing a portion of the product gas from (a) also containing steam, into contact with a shift conversion catalyst for the production of a gas composed primarily of hydrogen,
    (c) passing the remaining portion of the product gas from (a) to an acid gas scrubber to produce a purified stream of hydrogen and carbon monoxide,
    (d) passing the purified stream of hydrogen and carbon monoxide from (c) into contact with a methanol synthesis catalyst for the production of methanol,
    (e) subjecting air to rectification to produce a gas consisting essentially of oxygen and a separate gas consisting primarily of nitrogen,
    (f) introducing a portion of the gas stream consisting essentially of oxygen from step (e) into the partial oxidation zone as supplemental oxygen therefor in step (a),
    (g) introducing the gas consisting primarily of nitrogen from step (e) and the gas rich in hydrogen recovered from step (b) into an ammonia synthesis reactor to produce a gas rich in ammonia,
    (h) introducing the methanol product in step (d), the ammonia product of step (g), and a portion of the gas stream of oxygen from step (e), together with a nutrient solution and an initial charge of Hansanula polymorpha DL 1 yeast, into a fermenter for the production of single cell protein with the formation of by-product gases containing oxygen and $CO_2$,
    (i) passing the gases containing oxygen and $CO_2$ from step (h) to said partial oxidation step (a), to act as primary oxygen for the partial oxidation step (a) and as a temperature moderator therefor,
    (j) recovering from the fermenter in step (h), single cell protein as a product of the process.

2. A process as defined in claim 1 in which steam in step (b) is provided by quenching the hot partial oxidation product with water.

3. A process as defined in claim 1 in which said nutrient solution in step (h) comprises $4.45 \times 10^5$ kg/day of water and $0.10 \times 10^5$ kg/day of salts, said salts comprising 1700 kg/day of KCl, 8500 kg/day of 85% solution of $H_3PO_4$, 400 kg/day of $Na_3SO_4$, 15 kg/day of $FeSO_4 \cdot 7H_2O$, 300 kg/day of $MgSO_4 \cdot 7H_2O$, 15 kg/day of $MnSO_4 \cdot 7H_2O$, 1.0 kg/day of $CaCl_2$, 200 grams/day of $ZnSO_4$, 200 grams/day of $H_3BO_3$, 200 grams/day of $CuSO_4 \cdot 0.5H_2O$, 40 grams/day of $Na_2MoO_4 \cdot 7H_2O$ and 6 grams/day of $NiCl_2 \cdot 0.6H_2O$.

4. A process as defined in claim 1 in which said methanol concentration in said fermenter, step (h), does not exceed 0.5 gram/liter.

5. A process as defined in claim 1 in which said carbonaceous fuel containing toxic inorganic and/or carcinogenic organic substances is subjected to partial oxidation to destroy the carcinogenic organic compounds and to recover as products a separate gaseous stream containing carbon monoxide and hydrogen, and a separate condensed stream containing toxic inorganic material.

6. A process as defined in claim 1 in which said carbonaceous fuel in step (a) comprises a liquid hydrogen fuel and a solid hydrocarbon fuel.

* * * * *

UNITED STATES PATENT AND TRADEMARK OFFICE
CERTIFICATE OF CORRECTION

PATENT NO. : 4,242,458
DATED : December 30, 1980
INVENTOR(S) : E. T. Child, R. M. Suggitt It is certified that error appears in the above—identified patent and that said Letters Patent is hereby corrected as shown below:

Col.8, line 64: "$SO_4 0.7H_2 0$" should read -- $SO_4.7H_2 0$ --

Col.8, line 64: "$MgSO_4 0.7H_2 0$" should read -- $MgSO_4.7H_2 0$ --

Col.8, line 65: "$MnSO_4 0.7H_2 0$" should read -- $MnSO_4.7H_2 0$ --

Col.8, line 67: "$CuSO_4 0.5H_2 0$" should read -- $CuSO_4.5H_2 0$ --

Col.8, line 67: "$Na_2 MoO_4 0.7H_2 0$" should read -- $Na_2 MoO_4.7H_2 0$ --

Col.8, line 68: "$NiCl_2 0.6H_2 0$" should read -- $NiCl_2.6H_2 0$ --

Col.10, line 5: "hydrogen" should read -- hydrocarbon --

Signed and Sealed this

Twenty-ninth Day of September 1981

[SEAL]

Attest:

Attesting Officer

GERALD J. MOSSINGHOFF

Commissioner of Patents and Trademarks